US011134851B2

United States Patent
Houck et al.

(10) Patent No.: US 11,134,851 B2
(45) Date of Patent: Oct. 5, 2021

(54) SENSOR DEVICE

(71) Applicant: VIAVI Solutions Inc., San Jose, CA (US)

(72) Inventors: William D. Houck, Santa Rosa, CA (US); Marc K. Von Gunten, Novato, CA (US)

(73) Assignee: VIAVI Solutions Inc., San Jose, CA (US)

( * ) Notice: Subject to any disclaimer, the term of this patent is extended or adjusted under 35 U.S.C. 154(b) by 236 days.

(21) Appl. No.: 16/220,718

(22) Filed: Dec. 14, 2018

(65) Prior Publication Data
US 2020/0187794 A1    Jun. 18, 2020

(51) Int. Cl.
| | | |
|---|---|---|
| *A61B 5/0205* | (2006.01) | |
| *A61B 5/00* | (2006.01) | |
| *A61B 5/01* | (2006.01) | |
| *A61B 5/02* | (2006.01) | |
| *A61B 5/024* | (2006.01) | |
| *A61B 5/026* | (2006.01) | |

(52) U.S. Cl.
CPC ........ *A61B 5/02055* (2013.01); *A61B 5/0059* (2013.01); *A61B 5/01* (2013.01); *A61B 5/02007* (2013.01); *A61B 5/0261* (2013.01); *A61B 5/02416* (2013.01); *A61B 5/6802* (2013.01)

(58) Field of Classification Search
CPC ..... A61B 5/02055; A61B 5/0059; A61B 5/01; A61B 5/02007; A61B 5/02416; A61B 5/0261; A61B 5/6802
See application file for complete search history.

(56) References Cited

U.S. PATENT DOCUMENTS

| | | | | |
|---|---|---|---|---|
| 2002/0183624 A1* | 12/2002 | Rowe | ..................... | A61B 5/681 600/476 |
| 2015/0201854 A1* | 7/2015 | Hong | .................. | A61B 5/0002 600/301 |
| 2015/0342527 A1 | 12/2015 | Karnik et al. | | |

(Continued)

FOREIGN PATENT DOCUMENTS

WO    2019025138 A1    2/2019

OTHER PUBLICATIONS

International Search Report and Written Opinion for Application No. PCT/US2019/065453, dated Jun. 25, 2020, 19 pages.

(Continued)

*Primary Examiner* — Lindsey G Wehrheim
(74) *Attorney, Agent, or Firm* — Harrity & Harrity, LLP

(57) ABSTRACT

A multi-sensor device may perform an optical measurement using an optical sensor of the multi-sensor device, where the optical measurement is performed when a surface of the multi-sensor device is in contact with a human body. The multi-sensor device may perform another measurement using at least one other sensor of the multi-sensor device, where the other measurement is performed when the surface of the multi-sensor device is in contact with the human body, where the other measurement is performed substantially contemporaneously with the optical measurement, and where the optical measurement and the other measurement relate to health parameters. The multi-sensor device may determine a combined measurement value based on the optical measurement and the other measurement.

20 Claims, 7 Drawing Sheets

(56) References Cited

U.S. PATENT DOCUMENTS

| | | | |
|---|---|---|---|
| 2016/0029911 A1* | 2/2016 | Lee | A61B 5/681 |
| | | | 600/301 |
| 2016/0313176 A1 | 10/2016 | Lee | |
| 2016/0374620 A1* | 12/2016 | Lisogurski | A61B 5/6838 |
| | | | 600/301 |
| 2017/0000415 A1* | 1/2017 | Lapetina | A61B 5/6843 |
| 2017/0049352 A1* | 2/2017 | Mirov | A61B 5/6824 |
| 2017/0086691 A1 | 3/2017 | Freschl et al. | |
| 2017/0325740 A1 | 11/2017 | Barnes et al. | |

OTHER PUBLICATIONS

Partial International Search Report for Application No. PCT/US2019/065453, dated Mar. 25, 2020, 15 pages.

\* cited by examiner

SENSOR DEVICE

BACKGROUND

A sensor device may perform measurements for various purposes. For example, an optical sensor may include an illuminator to provide light and a detector to detect the light. The optical sensor may determine a measurement based on characteristics of the light after the light interacts with a target. One example of such a target is the human body, for which an optical sensor may be used to determine health-related measurements.

SUMMARY

According to some implementations, a device may include an optical sensor, wherein the optical sensor is to perform an optical measurement when a surface of the device is in contact with a human body. The device may include a plurality of electrical probes provided in a housing or a barrier of the optical sensor, wherein the device is to perform an electrical measurement using the plurality of electrical probes when the surface of the device is in contact with the human body, wherein the electrical measurement is to be performed substantially contemporaneously with the optical measurement, and wherein the device is a handheld or wearable device.

According to some implementations, a handheld or wearable sensor device may include an optical sensor, wherein the optical sensor is to perform an optical health-related measurement when a surface of the handheld or wearable sensor device is in contact with a human body. The handheld or wearable sensor device may include at least one other sensor provided in a barrier or housing of the optical sensor, wherein the at least one other sensor is to perform another health-related measurement, substantially contemporaneously with the optical health-related measurement or with a known time offset from the optical health-related measurement, when the surface of the handheld or wearable sensor device is in contact with the human body.

According to some implementations, a method may be performed by a multi-sensor device and may include performing an optical measurement using an optical sensor of the multi-sensor device, wherein the optical measurement is performed when a surface of the multi-sensor device is in contact with a human body. The method may include performing another measurement using at least one other sensor of the multi-sensor device, wherein the other measurement is performed when the surface of the multi-sensor device is in contact with the human body, wherein the other measurement is performed substantially contemporaneously with the optical measurement, and wherein the optical measurement and the other measurement relate to health parameters. The method may include determining a combined measurement value based on the optical measurement and the other measurement.

DETAILED DESCRIPTION

Figure 1:
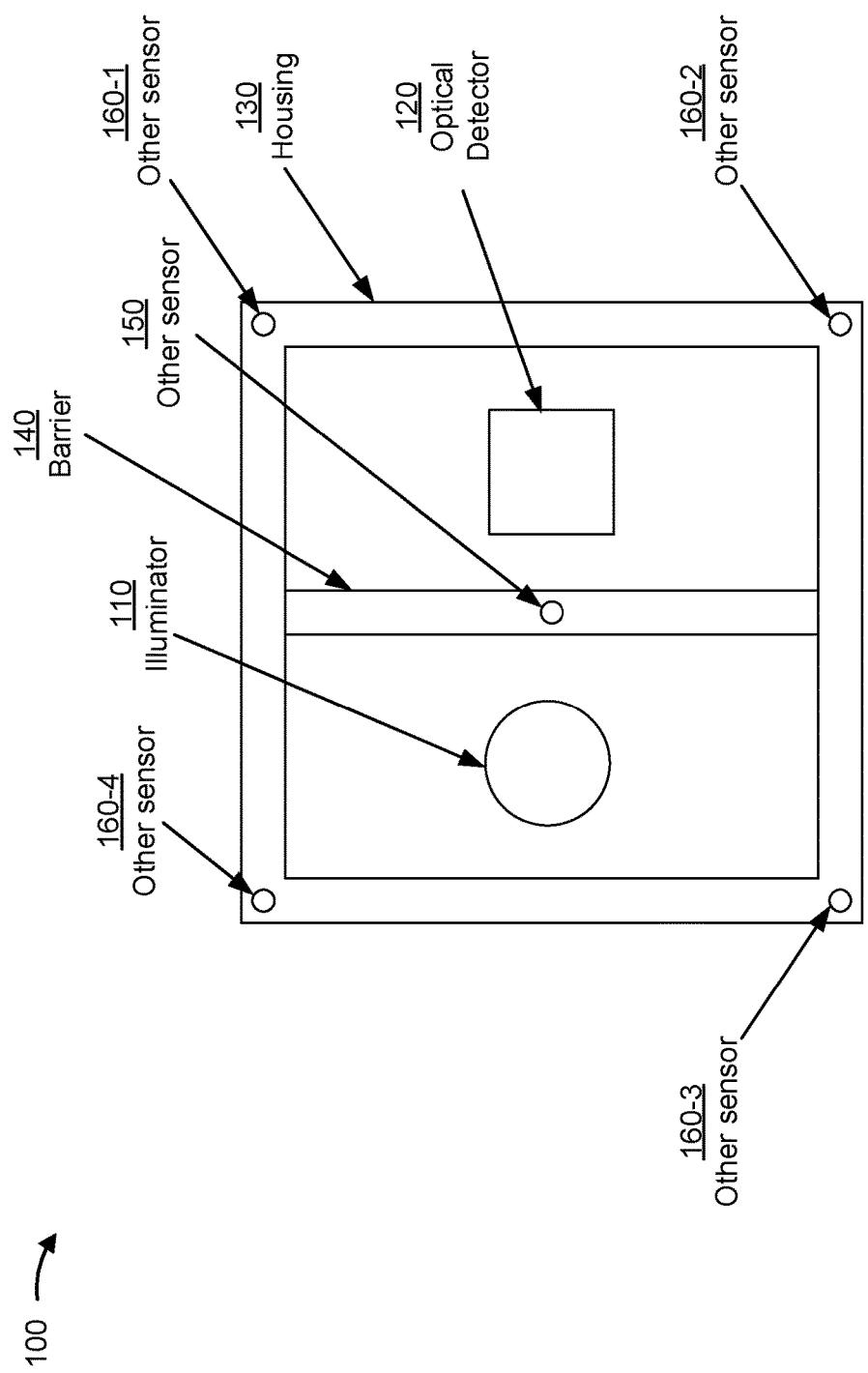
FIGS. 1-4 are diagrams of example implementations of a multi-sensor device described herein.

The following detailed description of example implementations refers to the accompanying drawings. The same reference numbers in different drawings may identify the same or similar elements.

An optical sensor may be used to determine an optical measurement. In some implementations, an optical sensor may be used to determine health-related measurements for a target. For example, a device (e.g., a handheld or portable device, a non-portable device, etc.) may include an optical sensor to determine health-related measurements or health parameters for a human body, such as heartbeat, blood pressure, or respiration rate. As used herein, a health parameter may be synonymous with a health-related measurement. However, a single optical sensor may only be able to perform a limited set of measurements, such as measurements that are based on optical features of the target. For example, some measurements may be difficult or impossible to perform optically, such as an electrical measurement, a pressure-based measurement, and/or the like.

Various combinations of measurements may be useful for health-related purposes. For example, it may be useful from a research perspective, a diagnosis perspective, a health monitoring perspective, and/or the like, to determine multiple measurements at a particular time and/or for a particular measurement target so that the multiple measurements are correlated with each other. As non-exhaustive examples: it may be useful to determine a blood glucose measurement that is correlated with another measurement (e.g., an optical measurement, such as heartbeat, blood pressure, respiration rate, etc.), or to determine a skin hydration or resistivity measurement that is correlated with another measurement (e.g., an optical measurement). These combinations of measurements may be particularly useful when correlation between the measurements is strong, such as when the measurements are obtained at substantially the same time and based on measuring substantially the same part of a target. It may be difficult or impossible to achieve satisfactory correlation levels when using multiple, separate sensor devices to determine the measurements. For example, when two measurements are determined by different sensor devices, the time relationship between the measurements may not be known at a sufficient level of precision to determine a correlation to a level required by an application, or the two measurements may be performed too far apart in time to determine a correlation to a level required by an application. As another example, when using two or more sensor devices, it may be difficult to ensure that a first measurement is performed with regard to the same part of a target as a second measurement, since a first sensor device must be removed from the target and a second, separate, sensor device must be placed on the target in the same location. This may cause imprecision, delay, and human error when determining combined measurements.

Some implementations described herein may provide a multi-sensor device that includes multiple, different sensors. For example, the multi-sensor device may include an optical sensor and another sensor. The other sensor may be provided in a housing or a barrier of the optical sensor. For example, the optical sensor may have a barrier to block an illuminator's light from being directly incident on a detector of the optical sensor, and may be at least partially enclosed in a housing. By being located in the barrier or the housing, the other sensor may be in contact with a target (e.g., a human body) at substantially the same time (or slightly before/after) and in substantially the same location as the optical sensor without using substantially more space or increasing the size of the sensor device in comparison to a device that includes only the optical sensor.

In this way, a combined measurement value may be determined by contemporaneously performing a first measurement using the optical sensor and a second measurement using the other sensor. "Contemporaneously" is defined in more detail elsewhere herein. In some cases, the optical sensor and the other sensor may be different types of sensors, which may enable the determination of combined measurement values that would not be possible or feasible using a single optical sensor. As just one example, the other sensor may be a temperature sensor, which may enable the determination of a plurality of vital signs (e.g., heartbeat, blood pressure, respiration rate, and body temperature) without successively applying different sensor devices to the human body. In some implementations, the other sensor may include, for example, a temperature sensor, an electrical sensor, a magnetic sensor, a microbolometer, a barometric sensor, an elasticity sensor, a pressure sensor, or another optical sensor (e.g., associated with a different detector material, a different size, etc.).

In this way, contemporaneous performance of multiple, different measurements on substantially the same part of a target is provided. This enables determination of combined measurement values at a higher level of accuracy or confidence (e.g., with a more robust correlation effect) than if the two sensors were applied to different regions of the target (e.g., spatially separated regions) or if the measurements were performed at different times (e.g., not contemporaneously, without a known or configured time offset, without a time offset that satisfies a threshold, etc.). For example, it may be difficult to determine a combined measurement using two separate sensor devices, since a user may not be capable of reliably aligning the two sensor devices on the same part of the target, and since the delay between the first measurement and the second measurement may reduce or eliminate useful correlation between the two measurements. Thus, correlation to a level required by a particular application may be achieved.

The multi-sensor device may have a single bus system, processor, electrical input/output structure, and/or the like, that can process a first measurement and a second measurement to determine the combined measurement while preserving the correlation between the first measurement and the second measurement (e.g., without introducing uncertainty regarding measurement times or locations), thus reducing manufacturing costs. Furthermore, utilizing previously unused areas of the multi-sensor device (e.g., the housing and/or the barrier) for additional sensors provides increased sensing capability within a compact size and further reducing costs relative to using multiple, different sensor devices or sensor packages.

FIG. 1 is a diagram of an overview of an example implementation 100 of a multi-sensor device described herein. As shown, the multi-sensor device includes an illuminator 110, an optical detector 120, a housing 130, a barrier 140, and/or other sensors 150, 160-1, 160-2, 160-3, and/or 160-4. Each is described in turn below. In some implementations, the multi-sensor device may be provided in a wearable device (e.g., a smart watch, an armband, an adhesive patch, a clip-on fingertip device, etc.), a handheld device (e.g., a measurement device, a wand, etc.), a smartphone, a tablet, a user device, a desktop, a laptop, a home health station, and/or the like.

Figure 2:
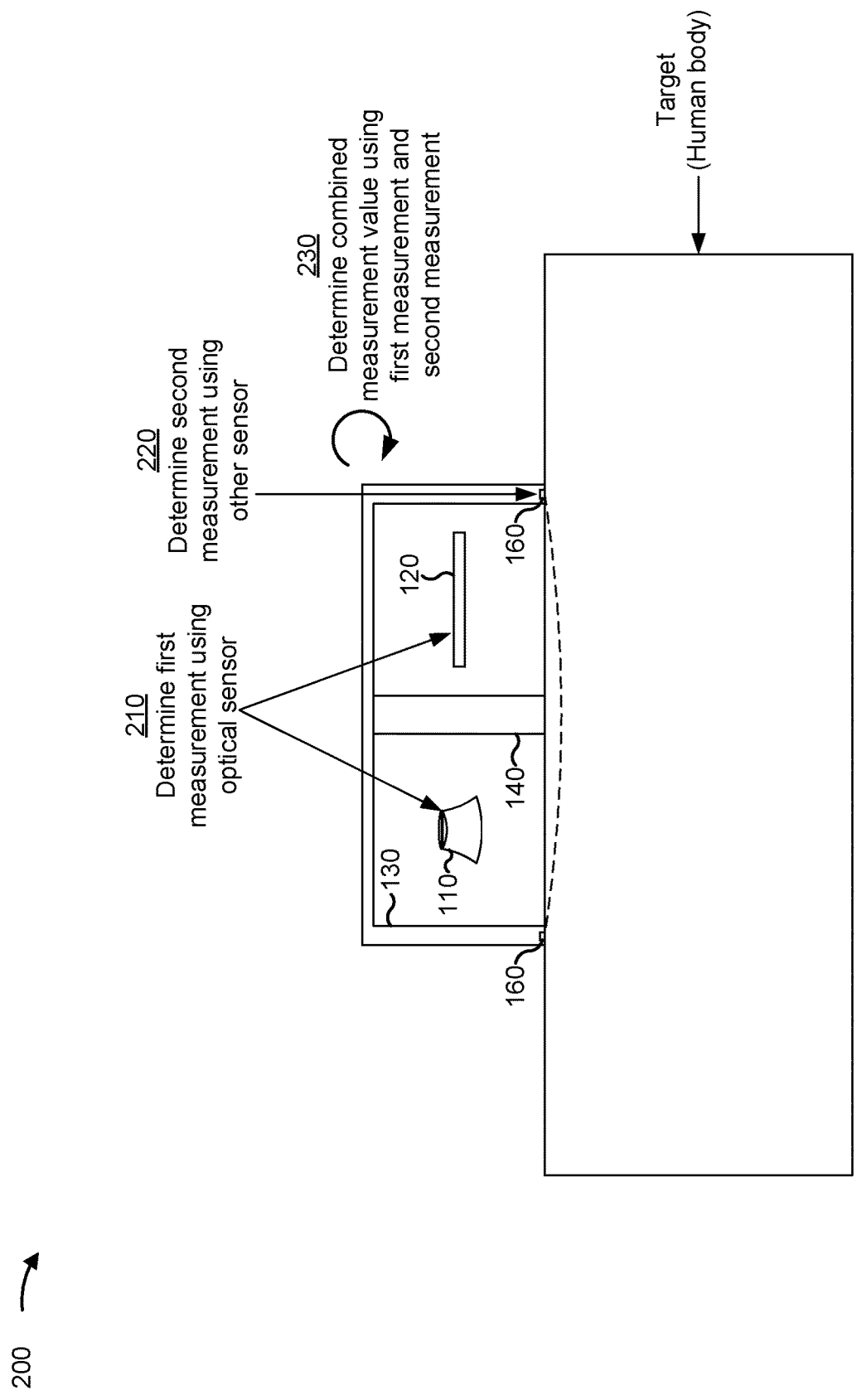
Figure 3:
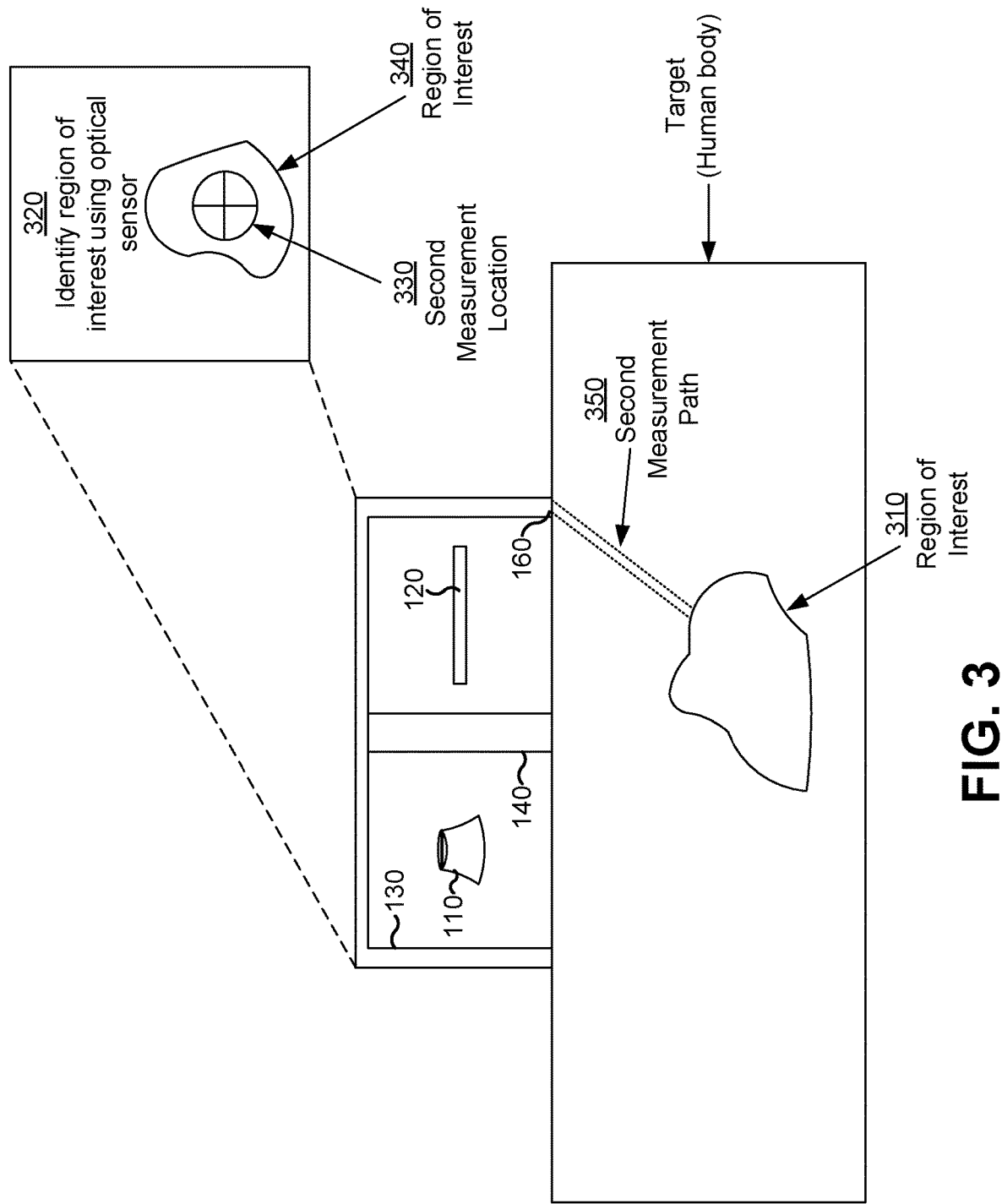

An optical sensor of the multi-sensor device may include one or more of illuminator 110, optical detector 120, housing 130, and/or barrier 140. Illuminator 110 includes a light source, such as a light emitting diode, a tungsten filament lamp, and/or the like. Illuminator 110 may provide light for an optical measurement to be performed using optical detector 120. For example, when a surface of the multi-sensor device is in contact with a target (e.g., a human body), the light provided by illuminator 110 may reflect from and/or transit through the target to optical detector 120. In some implementations, the light may transmit to optical detector 120 through a window, such as a window aperture of the optical sensor. In some implementations, the window may be provided parallel to a surface of the device that is to contact the target. In FIG. 1, the surface that is to contact the target is parallel to the plane of the page of FIG. 1 (i.e., is facing the reader). In FIGS. 2 and 3, described in more detail below, the surface that is to contact the target is perpendicular to the planes of the pages of FIGS. 2 and 3.

Optical detector 120 may include a photodetector, a photosensor, an imaging sensor, an image sensor, an imager, a semiconductor charge-coupled device (CCD) sensor, a complimentary metal-oxide-semiconductor (CMOS) sensor, and/or the like. In some implementations, optical detector 120 may be associated with a single wavelength. In some implementations, optical detector 120 may be associated with multiple wavelengths (e.g., may be a multispectral optical detector). In some implementations, optical detector 120 may include or be associated with a filter, such as a filter for a single wavelength or for multiple, different wavelengths. For example, the filter may filter light from the target to a particular wavelength or wavelength range to enable measurement of the particular wavelength or wavelength range. In some implementations, the filter may include multiple, different regions so that different measurements can be performed using optical detector 120.

In some implementations, the optical sensor may determine an image-based measurement or an image using optical detector 120. In such a case, the multi-sensor device may use an image, determined by optical detector 120, to configure, align, and/or perform a measurement using another sensor, as described in more detail below.

The optical sensor may determine a measurement using optical detector 120. For example, the multi-sensor device or a control device associated with the multi-sensor device may determine a measurement value based on an electrical signal generated by one or more pixels of optical detector 120. The one or more pixels may be associated with (e.g., included in, identified by) a region of interest. In some implementations, the optical sensor (e.g., the multi-sensor device or the control device) may determine multiple, different measurement values (e.g., using multiple sets of pixels of optical detector 120). For example, the optical sensor may determine multiple, different measurement values for respective regions of interest. Thus, optical detector 120 may perform multiple, different measurements using a single optical sensor.

Housing 130 provides a physical shell (e.g., enclosure, wall, sensor package, etc.) that at least partially encloses illuminator 110 and/or optical detector 120. Housing 130 may be composed of any suitable material, such as a polymer and/or the like. Barrier 140 may be provided between illuminator 110 and optical detector 120. Barrier 140 may absorb light from illuminator 110 that is not incident on the target, in order to prevent unwanted light from reaching optical detector 120 and causing noise in a measurement performed by the optical sensor. In some implementations, barrier 140 may be a part of housing 130. In some implementations, the multi-sensor device may not include a barrier. In some implementations, barrier 140 may extend from housing 130 to the surface of the multi-sensor device. In some implementations, barrier 140 may partially extend from housing 130 to the surface (e.g., may stop short of the surface).

As shown, in some implementations, one or more other sensors 150 may be provided in barrier 140. Here, other sensor 150 is provided approximately in a center of barrier 140, although other sensor 150 may be provided in any location in barrier 140. Other sensor 150 may include any sensor described herein other than optical detector 120. Other sensor 150 may be provided on or in a surface of the multi-sensor device so that other sensor 150 is in contact with a target when the surface of the multi-sensor device is in contact with the target. Thus, contemporaneous measurement using the optical sensor and other sensor 150 is enabled. In some implementations, other sensor 150 may be provided within barrier 140 (e.g., with a light pipe or other device to enable measurement of the target), as described in more detail elsewhere herein.

As shown, in some implementations, one or more other sensors 160 may be provided in housing 130. Here, other sensors 160 are provided at corners of housing 130, although other sensor 160 can be provided at any location in housing 130. Other sensor 160 may include any sensor described herein other than optical detector 120. Other sensor 160 may be provided at a surface of the multi-sensor device so that other sensor 160 is in contact with a target when the surface of the multi-sensor device is in contact with the target. In some implementations, other sensor 160 may be provided within housing 130 (e.g., with a light pipe or another device to enable measurement of the target). Thus, contemporaneous measurement using the optical sensor and other sensor 160 is enabled.

In some aspects, other sensor 150 and/or other sensor 160 (collectively referred to herein as other sensor 150/160) may include one or more electrical probes. For example, an electrical probe may be used to determine an electrical measurement such as a resistance measurement, a resistivity measurement, a hydration measurement, a conductivity measurement, and/or the like. In such a case, other sensor 150/160 may include at least one electrical probe to provide an electrical signal and at least one electrical probe (e.g., a sensor, a readout pad, an onboard electronic system, etc.) to determine a measurement based on the electrical signal. In some aspects, other sensor 150/160 may include at least two electrical probes, which may be located at different locations on or in the surface of the multi-sensor device. In this way, the multi-sensor device may determine measurements using different combinations of the electrical probes, which may provide improved measurement accuracy and flexibility in comparison to performing the measurement using a single electrical probe. For example, the multi-sensor device may determine a first resistance measurement using a first pair of electrical probes, and may determine a second resistance measurement using a second pair of electrical probes, wherein the first pair of electrical probes is different than the second pair of electrical probes.

In some aspects, other sensor 150/160 may include one or more temperature sensors (e.g., a thermocouple, a resistance temperature detector, a thermistor, a thermopile, etc.). In this case, other sensor 150/160 may be used in conjunction with the optical sensor to provide a vital signs measurement set, wherein the vital signs measurement set is defined as the physiologic heartbeat, blood pressure, respiration rate, and body temperature of the target. For example, heartbeat, blood pressure, and respiration rate may be measured using the optical sensor (e.g., through analysis of the photoplethysmograph). By combining heartbeat, blood pressure, and respiration rate measurement values with a body temperature measurement determined using other sensor 150/160 to determine a combined measurement value, the multi-sensor device may determine a more complete and accurate vital signs measurement, since the combined measurement value may be more accurate than a vital signs measurement value that is determined using sensors that are in contact with the target at different times and/or in different locations.

In some implementations, other sensor 150/160 may include a second optical sensor. For example, the optical sensor (e.g., the optical sensor that includes illuminator 110 and optical detector 120) may be a first optical sensor and other sensor 150/160 may be a second optical sensor. In some implementations, the first optical sensor and the second optical sensor may use the same illuminator (e.g., illuminator 110) which may reduce cost and package size in comparison to using separate illuminators. In some implementations, the first optical sensor and the second optical sensor may use different illuminators, which may provide increased flexibility with regard to possible combinations of measurements to be performed by the first optical sensor and the second optical sensor since the different illuminators can provide different wavelengths or intensities of light.

In some implementations, the first optical sensor may be associated with a first optical detector (e.g., optical detector 120) and the second optical sensor may be associated with a second optical detector. In some implementations, the first optical detector may be a different size and/or fabricated of a different material than the second optical detector. For example, the first optical detector may be larger than the second optical detector. As another example, the first optical detector may be fabricated of a first material and the second optical detector may be fabricated of a second material that is more expensive than the first material. In this case, the second optical detector may be smaller than the first optical sensor (e.g., approximately 8 microns wide, approximately 10 microns wide, etc.), which may reduce cost associated with using the more expensive material. In some implementations, the first material may be silicon. In some implementations, the second material may be a different material than the first material, such as a phosphide (e.g., InP, GaP, AlP, AlInGaP, etc.) and/or the like. Furthermore, when the first optical detector and the second optical detector are fabricated from different materials, a wider range of measurements may be performed than when both optical detectors are fabricated from the same material. For example, a material associated with a first spectral range (e.g., a range of approximately 400 nm to 1100 nm) may be used for the first optical detector, and a material associated with a second spectral range (e.g., a range with a lower bound greater than approximately 2500 nm) may be used for the second optical detector. In this case, the smaller size of the second optical detector may reduce cost of the multi-sensor device while providing measurement capability in the second spectral range. This may be particularly useful, for example, for blood sugar or glucose measurements, which can be measured more accurately in the >2500 nm range than in the 400-1100 nm range.

In some implementations, other sensor 150/160 may comprise a magnetic sensor, a barometric sensor, an elasticity sensor (e.g., a pressure sensor, a stress sensor, a strain sensor, and/or the like), a microbolometer, and/or the like. Such a sensor may provide for the contemporaneous determination of non-optical measurements and optical measurements. For example, optical measurements may not be capable of accurately measuring some parameters, due to lack of an optical signal relating to such a parameter and/or due to complex confounding of the signal in the optical measurement pathway. Other sensor 150/160 may provide for the contemporaneous measurement of such parameters using non-optical measurements, thereby improving the versatility of the multi-sensor device.

In some implementations, other sensor 150/160 may include multiple sensors of different types. In this case, multiple measurements of different types may be obtained substantially contemporaneously and/or with regard to the same contact area of the target. Thus, combined measurement values may be determined using the optical sensor and the other sensors 150/160, which may not be possible or feasible when the sensors are provided in different packages.

In some implementations, the optical sensor may perform a measurement based on other sensor 150/160 or based on a measurement of other sensor 150/160. For example, other sensor 150/160 may include a set of electrical probes. In such a case, the optical sensor may perform a measurement based on a resistance or conductivity measurement determined by the set of electrical probes. For example, the optical sensor may perform the measurement when the resistance or conductivity measurement indicates that the optical sensor is in contact with the target (e.g., when the resistance or conductivity measurement satisfies a threshold). In some implementations, other sensor 150/160 may perform a measurement based on the optical sensor or based on a measurement of the optical sensors. For example, other sensor 150/160 may perform a measurement when the optical sensor indicates that the multi-sensor device is in contact with the target. As another example, the optical sensor may be used to determine a region of interest for a measurement or to align other sensor 150/160 to perform a measurement, as described in more detail below in connection with FIG. 3.

In some cases, the optical sensor and the other sensor 150/160 are described herein as performing measurements contemporaneously or substantially contemporaneously. In some implementations, "contemporaneously" may refer to two measurements being performed simultaneously or substantially simultaneously. In some implementations, "contemporaneously" may refer to two measurements being performed with a brief (e.g., less than two seconds) time offset. For example, the multi-sensor device may be associated with a sampling rate, which may be defined in samples per second (sps). The multi-sensor device may determine measurements in accordance with the sampling rate, by determining sensor data on sampling events at the sampling rate. Two measurements may be said to be performed contemporaneously when the two measurements are performed on the same sampling event or within a particular number of sampling events of each other (e.g., within two sampling events, five sampling events, etc.). The particular number of sampling events divided by the sampling rate may be equal to the time offset.

When the measurements are performed contemporaneously, the multi-sensor device may correlate the measurements with each other more effectively than when the measurements are performed non-contemporaneously (e.g., using different sensor devices, at different times, for different regions of the target, etc.). In other words, it may be more difficult to correlate measurements performed by different sensor devices non-contemporaneously than it is to correlate measurements performed contemporaneously by a single sensor device (e.g., based on the different sensor devices possibly being misaligned in time, being associated with different sampling rates, being in contact with different parts of the target, etc.). Thus, more accurate correlative data capture may be performed using the implementations described herein than when non-contemporaneous measurement is performed.

In some implementations, the multi-sensor device may have a thickness of approximately 3 mm or in a range of approximately 1 mm to 5 mm, and a cross-sectional size of approximately 5 mm by approximately 8 mm. In some implementations, optical detector 120 may have a size of approximately 3 mm by approximately 3 mm or in a range of approximately 1 mm×1 mm to approximately 5 mm×5 mm. In some implementations, illuminator 110 may be placed in a range of approximately 3 mm to 5 mm from optical detector 120. In some implementations, the housing 130 and/or the barrier 140 may have a thickness in a range of approximately 0.5 mm to 1.5 mm.

As indicated above, FIG. 1 is provided merely as an example. Other examples may differ from what is described with regard to FIG. 1.

FIG. 2 is a diagram of an overview of an example implementation 200 described herein. As shown in FIG. 2, implementation 200 includes a multi-sensor device with an illuminator 110, an optical detector 120, a housing 130, a barrier 140, and one or more other sensors 160 provided on a surface of the multi-sensor device. In some implementations, the multi-sensor device may include one or more other sensors 150 (e.g., provided in the barrier 140) in addition to the one or more other sensors 160 or instead of the one or more other sensors 160. As shown, a surface of the multi-sensor device is in contact with a target. Here, the target is a human body. For example, the multi-sensor device may be in contact with a skin layer of the target or an internal surface of the target (e.g., an internal organ, a mouth, a sinus, etc.).

As shown in FIG. 2, and by reference number 210, the multi-sensor device may determine a first measurement using an optical sensor of the multi-sensor device (e.g., illuminator 110 and optical detector 120). In some implementations, a first measurement may include a health-related measurement or a health parameter. As used herein, a health-related measurement may be any measurement related to the human body that can be determined using one or more of the sensors described herein (e.g., a heartbeat measurement, a respiration rate measurement, a blood pressure measurement, a temperature measurement, a pressure measurement, a conductivity measurement, a hydration measurement, etc.). However, the implementations described herein are not limited to those in which the multi-sensor device captures health-related measurements. For example, one or more sensors of the multi-sensor device may be used to determine a measurement other than a health-related measurement, such as a measurement to determine when another measurement is to be performed, an imaging operation to identify a region of interest, and/or the like.

As shown by reference number 220, the multi-sensor device may determine a second measurement using the other sensor (e.g., other sensors 160). The second measurement may be a resistance measurement determined using other sensors 160, although any other measurement capable of being performed by the other sensors 150/160 may be performed as the second measurement. For example, the second measurement may include any health-related measurement or a different type of measurement (e.g., a measurement to determine that an optical measurement should be performed, etc.).

In some implementations, the multi-sensor device may determine the second measurement contemporaneously with the first measurement. For example, the multi-sensor device may determine the second measurement substantially simultaneously with the determination of the first measurement, or with a known offset (e.g., time offset, number of sampling events, etc.) from the first measurement. In some implementations, the multi-sensor device may determine the first measurement and the second measurement with regard to the same area of the target. For example, the multi-sensor device may determine the second measurement without moving (or being moved) relative to the target before or after determining the first measurement. Thus, correlation of the first measurement and the second measurement is improved relative to cases in which the first measurement and the second measurement might be determined using different sensor devices, at substantially different times, with regard to different locations of the target, and/or the like.

As shown by reference number 230, the multi-sensor device may determine a combined measurement value using the first measurement and the second measurement. In some implementations, a combined measurement value may include a combination of a first measurement value determined by the optical sensor and a second measurement value determined by the other sensor 150/160. For example, in the case wherein the other sensor 150/160 includes a set of electrical probes, the combined measurement value may identify hydration values in relation to an optical measurement (e.g., a blood pressure measurement, a heartbeat measurement, or a respiration rate measurement). As another example, in the case wherein the other sensor 150/160 includes a second optical sensor associated with a longer wavelength than the first optical sensor, the combined measurement may identify blood glucose levels in relation to a lower-wavelength optical measurement, such as a blood pressure measurement, a heartbeat measurement, or a respiration rate measurement.

Accurate combined measurement values using two or more different sensor devices are difficult to obtain. For example, uncertainty regarding particular times at which measurements are performed, locations at which the measurements are performed, and/or the like, may lead to unacceptable uncertainty in correlation between the measurements. By performing the measurements using a multi-sensor device with collocated sensors that perform the measurements in a contemporaneous fashion, uncertainty in the correlation between the measurements is reduced or eliminated. For example, the multi-sensor device may have a single bus system, processor, electrical input/output structure, and/or the like, that can process the first measurement and the second measurement to determine the combined measurement while preserving the correlation between the first measurement and the second measurement (e.g., without introducing uncertainty regarding measurement times or locations). Thus, measurements may be combined in ways that are difficult or impossible when performed with two or more different sensor devices.

As indicated above, FIG. 2 is provided merely as an example. Other examples may differ from what is described with regard to FIG. 2.

FIG. 3 is a diagram of an overview of an example implementation 300 described herein. FIG. 3 shows an example of identifying a region of interest for a measurement using an optical sensor of a multi-sensor device. The region of interest is located in or on the target, and is represented by the irregular shape shown by reference number 310. The region of interest may be a feature of the target, a particular layer of the target, an object included in the target (e.g., a tumor, a cyst, a blood vessel, etc.), and/or the like. In some implementations, the region of interest may be identifiable using the optical sensor (e.g., an imaging function of the optical sensor or a spectral or multispectral sensing function of the optical sensor).

As shown by reference number 320, the multi-sensor device may identify the region of interest using the optical sensor (e.g., the illuminator 110 and/or the optical detector 120). As shown by reference number 330, the multi-sensor device may indicate a location for a second measurement within the region of interest, shown by reference number 340. The second measurement may be a measurement to be performed by other sensor 160 and/or other sensor 150 (not shown).

In some implementations, the multi-sensor device may provide information indicating the location for the second measurement. For example, the multi-sensor device, and/or a control device associated with the multi-sensor device, may provide, for display, a user interface. The user interface may identify the location for the second measurement with regard to the region of interest. For example, the user interface may indicate the location of the second measurement (shown here using a crosshair), which may permit a user to align the second measurement to be performed with regard to the region of interest or a desired portion of the region of interest.

In some implementations, the multi-sensor device may indicate the location of the second measurement based on a path of the second measurement, shown by reference number 350. For example, the path of the second measurement may be associated with a particular spatial relationship with the optical sensor (e.g., a particular angular offset, a particular depth in the target, a particular length of the path, a particular size of a measurement area, etc.). The multi-sensor device may determine the location of the second measurement based on the particular spatial relationship. Thus, the optical sensor may be used to align or perform the second measurement using the other sensor, which improves accuracy and versatility of the second measurement.

In some implementations, the optical sensor may be associated with a wavelength that at least partially penetrates the target. For example, and as shown in FIG. 3, in some cases, the region of interest may be located below a surface of the target. In this case, the optical sensor may be associated with a wavelength that penetrates to the region of interest. Thus, the optical sensor may be used for subsurface alignment of the second measurement with a region of interest that may not be visible at the surface of the target. This may be particularly useful for measurements that are to be performed on a small or irregularly shaped subsurface region of interest, such as a blood vessel or a small irregularity.

The example shown in FIG. 3 relates to an implementation wherein a user interface is provided to indicate the location of the second measurement. In some implementations, the multi-sensor device may automatically determine the location of the second measurement. For example, the multi-sensor device may use the optical measurement to determine a location of the region of interest, and may perform the second measurement with regard to the region of interest. As another example, the multi-sensor device may identify the region of interest based on the optical measurement (e.g., based on an optical response of the optical detector 120, based on an optical response of pixels of the optical detector 120 that are in the region of interest in comparison to an optical response of pixels of the optical detector 120 for another region, etc.), and may automatically perform the second measurement with regard to the region of interest. Thus, the optical detector may be used to identify a region of interest and automatically perform a second measurement with regard to the region of interest, which may improve accuracy and reduce delay in performing the second measurement in comparison to performing the second measurement based on human input, thereby improving correlation of the optical measurement and the second measurement.

As indicated above, FIG. 3 is provided merely as an example. Other examples may differ from what is described with regard to FIG. 3.

Figure 4:
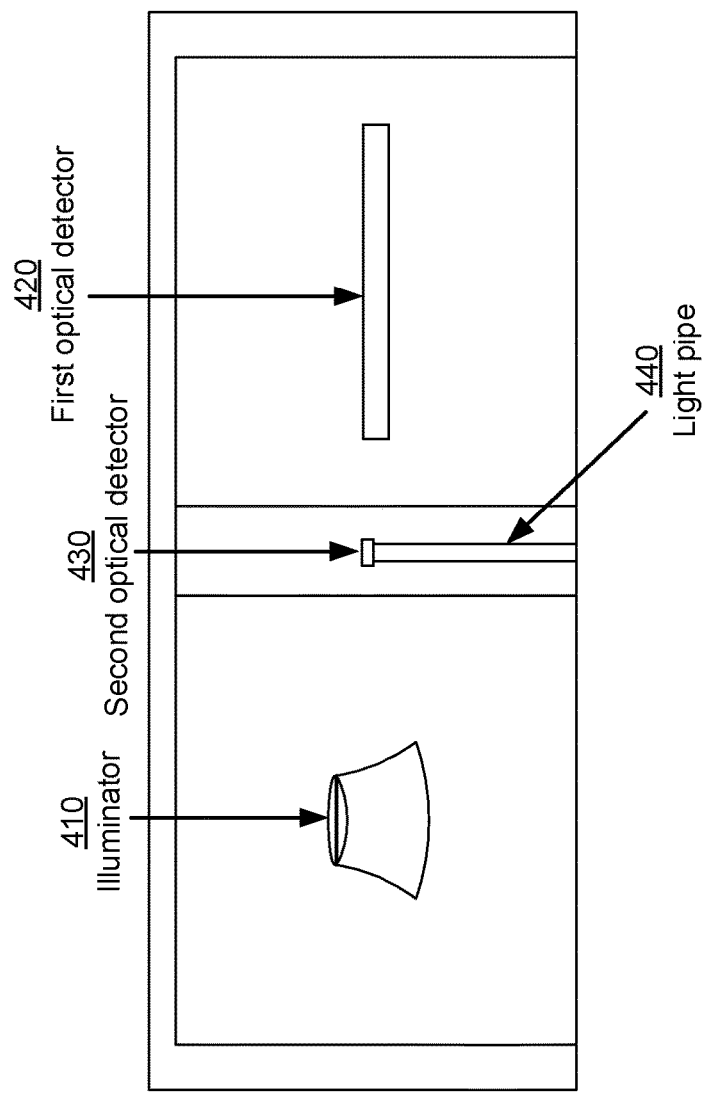

FIG. 4 is a diagram of an overview of an example implementation 400 described herein. FIG. 4 shows an example implementation of a multi-sensor device with a first optical sensor and a second optical sensor. As shown, the multi-sensor device may include an illuminator 410 (e.g., illuminator 110), a first optical detector 420 (e.g., optical detector 120), a second optical detector 430, and a light pipe 440. Second optical detector 430 may include an imaging sensor (e.g., a semiconductor charge-coupled device (CCD) sensor, a complimentary metal-oxide-semiconductor (CMOS) sensor, and/or the like).

In some implementations, first optical detector 420 may be composed of a first material and second optical detector 430 may be composed of a second material. For example, the first material may be different than the second material. In some implementations, the first material may be less expensive and/or easier to fabricate than the second material. For example, the first material may be silicon and the second material may be another material. In some implementations, first optical detector 420 may be larger than second optical detector 430. For example, first optical detector 420 may include more pixels than second optical detector 430, may have a larger cross-sectional area than second optical detector 430, and/or the like. As another example, second optical detector 430 may be approximately 8 microns in width, approximately 10 microns in width, and/or the like. In such a case, and when the two optical detectors are composed of different materials, cost savings may be achieved in comparison to having two optical detectors of equal size, while still providing the increased flexibility and sensing range of second optical detector 430.

In some implementations, first optical detector 420 may be associated with a first spectral range and second optical detector 430 may be associated with a second spectral range different than the first spectral range. For example, second optical detector 430 may perform a measurement that is associated with an optical effect outside the first spectral range, thus increasing the versatility of the multi-sensor device while reducing cost in comparison to having two equally-sized optical detectors in the multi-sensor device.

Light pipe 440 may include an optical device to transmit light from the surface of the multi-sensor device to second optical detector 430. For example, light pipe 440 may include an optical fiber, a waveguide, and/or the like. In some implementations, the multi-sensor device may not include light pipe 440. For example, second optical detector 430 may be provided at a surface of the multi-sensor device, in an enclosure with first optical detector 420, and/or the like.

In some implementations, second optical detector 430 may perform a measurement using illuminator 410. For example, first optical detector 420 and second optical detector 430 may use the same illuminator, which may reduce size and cost of the multi-sensor device. In some implementations, first optical detector 420 and second optical detector 430 may be associated with respective illuminators. For example, first optical detector 420 may use illuminator 410 and second optical detector 430 may use another illuminator (not shown in FIG. 4). In such a case, the other illuminator may be associated with a different spectral range than illuminator 410, which may improve flexibility of the multi-sensor device.

As indicated above, FIG. 4 is provided merely as an example. Other examples may differ from what is described with regard to FIG. 4.

Figure 5:
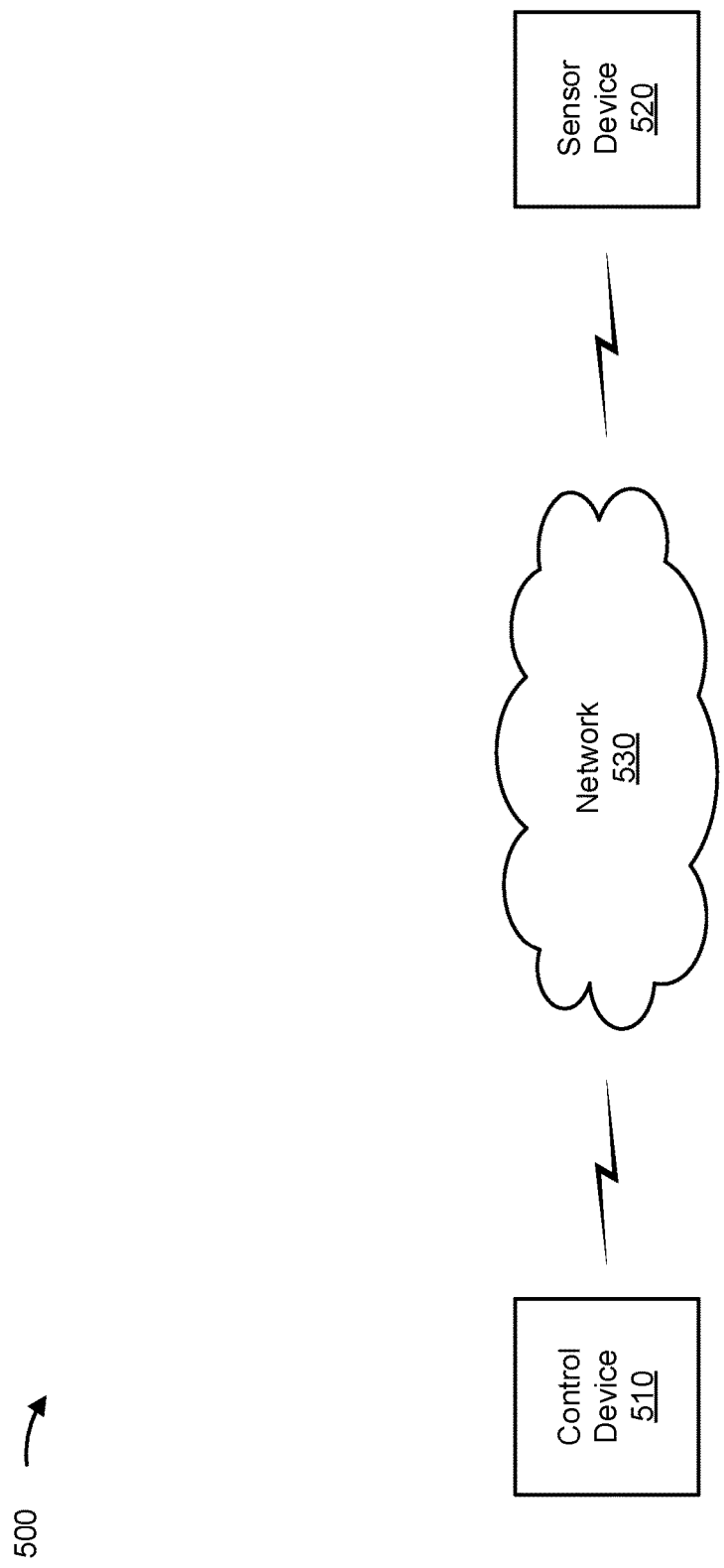
FIG. 5 is a diagram of an example environment in which systems and/or methods, described herein, may be implemented.

FIG. 5 is a diagram of an example environment 500 in which systems and/or methods, described herein, may be implemented. As shown in FIG. 5, environment 500 may include a control device 510, a multi-sensor device 520, and a network 530. Devices of environment 500 may interconnect via wired connections, wireless connections, or a combination of wired and wireless connections.

Control device 510 includes one or more devices capable of storing, processing, and/or routing information associated with sensing. For example, control device 510 may include a server, a computer, a wearable device, a cloud computing device, and/or the like. In some implementations, control device 510 may be associated with a particular multi-sensor device 520. In some implementations, control device 510 may be associated with multiple multi-sensor devices 520. In some implementations, control device 510 may receive information from and/or transmit information to another device in environment 500, such as multi-sensor device 520.

Multi-sensor device 520 includes a device capable of performing contemporaneous measurements using an optical sensor and one or more other sensors. Multi-sensor device 520 may include an optical sensor and one or more other sensors that can perform contemporaneous measurements when multi-sensor device 520 is in contact with a target. In some implementations, multi-sensor device 520 may include one or more components to receive, determine and/or process measurements performed by sensors of multi-sensor device 520, such as an input/output component (e.g., an electrical input/output component for the sensors), a bus (e.g., a bus to carry sensor data), a processor to process the sensor data, and/or the like. In some implementations, multi-sensor device 520 may be a handheld or wearable device or may be included in a handheld or wearable device.

Network 530 includes one or more wired and/or wireless networks. For example, network 530 may include a cellular network (e.g., a long-term evolution (LTE) network, a code division multiple access (CDMA) network, a 3G network, a 5G network, a 6G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 5 are provided as an example. In practice, there may be additional devices and/or networks, fewer devices and/or networks, different devices and/or networks, or differently arranged devices and/or networks than those shown in FIG. 5. Furthermore, two or more devices shown in FIG. 5 may be implemented within a single device, or a single device shown in FIG. 5 may be implemented as multiple, distributed devices. Additionally, or alternatively, a set of devices (e.g., one or more devices) of environment 500 may perform one or more functions described as being performed by another set of devices of environment 500.

Figure 6:
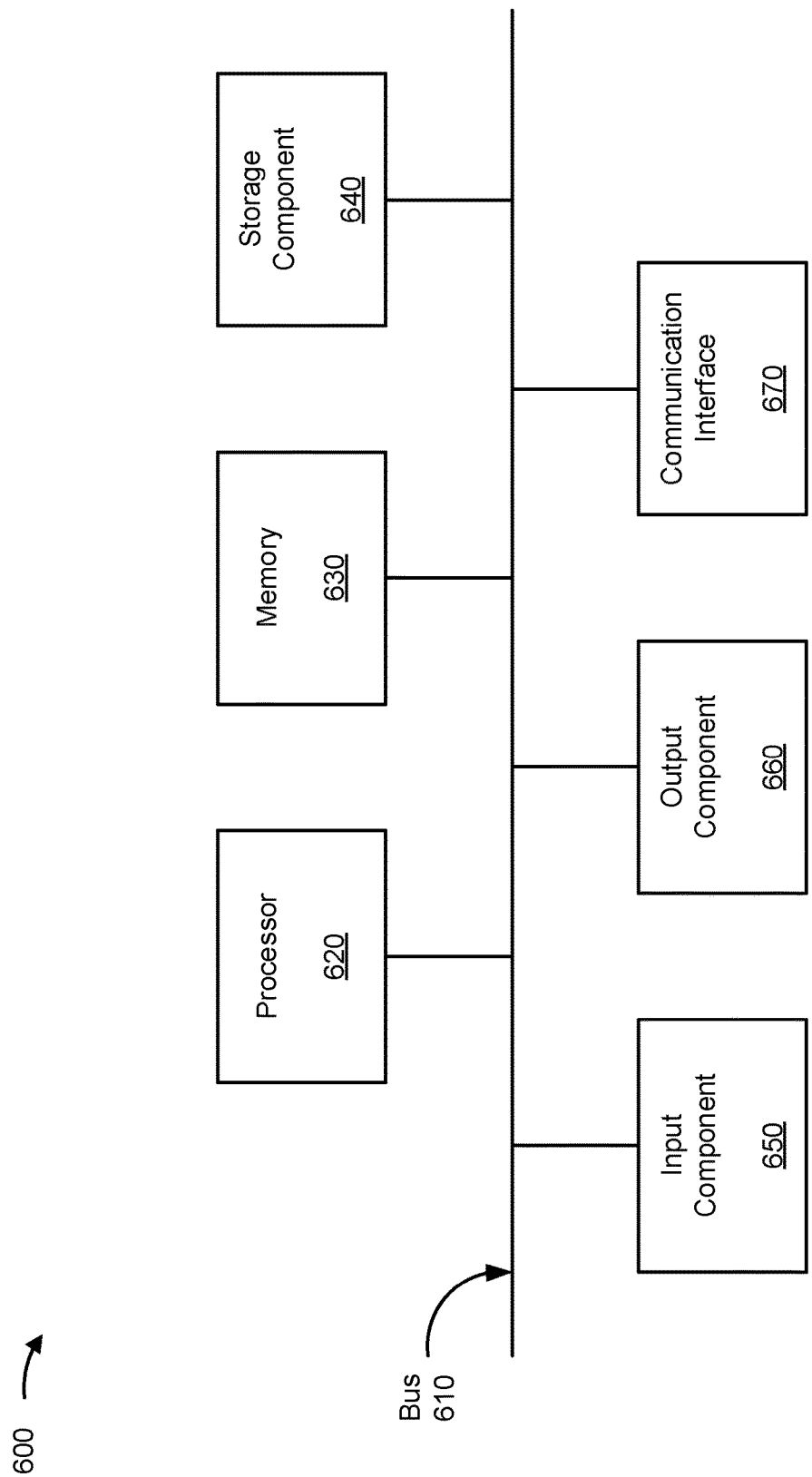
FIG. 6 is a diagram of example components of one or more devices of FIG. 5.

FIG. 6 is a diagram of example components of a device 600. Device 600 may correspond to control device 510 and/or multi-sensor device 520. In some implementations, control device 510 and/or multi-sensor device 520 may include one or more devices 600 and/or one or more components of device 600. As shown in FIG. 6, device 600 may include a bus 610, a processor 620, a memory 630, a storage component 640, an input component 650, an output component 660, and/or a communication interface 670.

Bus 610 includes a component that permits communication among the components of device 600. Processor 620 is implemented in hardware, firmware, or a combination of hardware and software. Processor 620 takes the form of a central processing unit (CPU), a graphics processing unit (GPU), an accelerated processing unit (APU), a microprocessor, a microcontroller, a field-programmable gate array (FPGA), an application-specific integrated circuit (ASIC), or another type of processing component. In some implementations, processor 620 includes one or more processors capable of being programmed to perform a function. Memory 630 includes a random access memory (RAM), a read only memory (ROM), and/or another type of dynamic or static storage device (e.g., a flash memory, a magnetic memory, and/or an optical memory) that stores information and/or instructions for use by processor 620.

Storage component 640 stores information and/or software related to the operation and use of device 600. For example, storage component 640 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 650 includes a component that permits device 600 to receive information, such as via user input (e.g., a touch screen display, a keyboard, a keypad, a mouse, a button, a switch, and/or a microphone). Additionally, or alternatively, input component 650 may include a sensor for sensing information (e.g., a global positioning system (GPS) component, an accelerometer, a gyroscope, an actuator, an optical sensor, and/or another form of sensor described herein). Output component 660 includes a component that provides output information from device 600 (e.g., a display, a speaker, and/or one or more light-emitting diodes (LEDs)).

Communication interface 670 includes a transceiver-like component (e.g., a transceiver and/or a separate receiver and transmitter) that enables device 600 to communicate with other devices, such as via a wired connection, a wireless connection, or a combination of wired and wireless connections. Communication interface 670 may permit device 600 to receive information from another device and/or provide information to another device. For example, communication interface 670 may include an Ethernet interface, an optical interface, a coaxial interface, an infrared interface, a radio frequency (RF) interface, a universal serial bus (USB) interface, a Wi-Fi interface, a cellular network interface, or the like.

Device 600 may perform one or more processes described herein. Device 600 may perform these processes based on processor 620 executing software instructions stored by a non-transitory computer-readable medium, such as memory 630 and/or storage component 640. A computer-readable medium is defined herein as a non-transitory memory device. A memory device includes memory space within a single physical storage device or memory space spread across multiple physical storage devices.

Software instructions may be read into memory 630 and/or storage component 640 from another computer-readable medium or from another device via communication interface 670. When executed, software instructions stored in memory 630 and/or storage component 640 may cause processor 620 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 6 are provided as an example. In practice, device 600 may include additional components, fewer components, different components, or differently arranged components than those shown in FIG. 6. Additionally, or alternatively, a set of components (e.g., one or more components) of device 600 may perform one or more functions described as being performed by another set of components of device 600.

Figure 7:
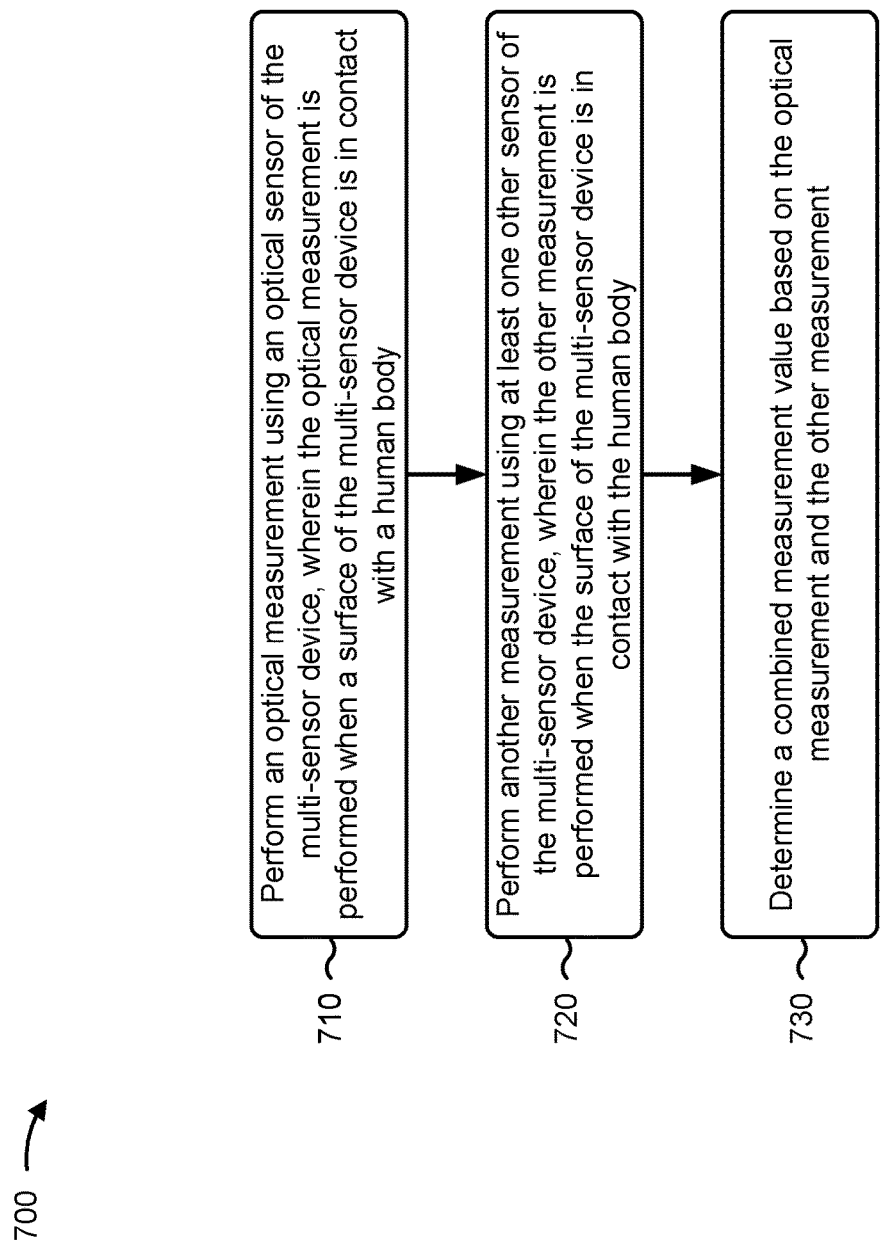
FIG. 7 is a flow chart of an example process for determining a combined measurement value using a multi-sensor device.

FIG. 7 is a flow chart of an example process 700 for determining a combined measurement value using a multi-sensor device. In some implementations, one or more process blocks of FIG. 7 may be performed by a multi-sensor device (e.g., multi-sensor device 520). In some implementations, one or more process blocks of FIG. 7 may be performed by another device or a group of devices separate from or including multi-sensor device 520, such as control device 510.

In some implementations, a device (e.g., the multi-sensor device 520) may include an optical sensor and may include a plurality of electrical probes provided in a housing or a barrier of the optical sensor, wherein the device is to perform an electrical measurement using the plurality of electrical probes when the surface of the device is in contact with the human body, wherein the electrical measurement is to be performed substantially contemporaneously with the optical measurement, and wherein the device is a handheld or wearable device.

In some implementations, a handheld or wearable sensor device (e.g., the multi-sensor device 520) may include the optical sensor, wherein the optical sensor is to perform an optical health-related measurement when a surface of the handheld or wearable sensor device is in contact with a human body, and may include at least one other sensor provided in a barrier or housing of the optical sensor, wherein the at least one other sensor is to perform another health-related measurement, substantially contemporaneously with the optical health-related measurement or with a known time offset from the optical health-related measurement, when the surface of the handheld or wearable sensor device is in contact with the human body.

As shown in FIG. 7, process 700 may include performing an optical measurement using an optical sensor of the multi-sensor device, wherein the optical measurement is performed when a surface of the multi-sensor device is in contact with a human body (block 710). For example, the multi-sensor device (e.g., using processor 620, memory 630, input component 650, and/or the like) may perform an optical measurement using an optical sensor of the multi-sensor device, as described above in connection with FIGS.

1-5. In some implementations, the optical measurement may be performed when a surface of the multi-sensor device is in contact with a human body.

As further shown in FIG. 7, process 700 may include performing another measurement using at least one other sensor of the multi-sensor device, wherein the other measurement is performed when the surface of the multi-sensor device is in contact with the human body (block 720). For example, the multi-sensor device (e.g., using processor 620, memory 630, input component 650, and/or the like) may perform another measurement using at least one other sensor of the multi-sensor device, as described above in connection with FIGS. 1-5. In some implementations, the other measurement may be performed when the surface of the multi-sensor device is in contact with the human body, the other measurement may be performed substantially contemporaneously with the optical measurement, and the optical measurement and the other measurement may relate to health parameters.

As further shown in FIG. 7, process 700 may include determining a combined measurement value based on the optical measurement and the other measurement (block 730). For example, the multi-sensor device (e.g., using processor 620, memory 630, storage component 640, input component 650, and/or the like) may determine a combined measurement value based on the optical measurement and the other measurement, as described above in connection with FIGS. 1-5.

Process 700 may include additional implementations, such as any single implementation or any combination of implementations described below and/or in connection with one or more other processes described elsewhere herein.

In some implementations, the multi-sensor device may identify a region of interest for the other measurement using the optical measurement, where the other measurement is performed with regard to the region of interest. In some implementations, the optical measurement and the other measurement may be performed based on a time offset between the optical measurement and the other measurement or a configurable time window in which the optical measurement and the other measurement are to be performed.

In some implementations, performing the other measurement may be based on the optical measurement. In some implementations, the multi-sensor device may determine that the surface of the multi-sensor device is in contact with the human body using the at least one other sensor, and performing the optical measurement may be based on determining that the surface of the multi-sensor device is in contact with the human body.

In some implementations, the electrical measurement may be a hydration measurement or a resistance measurement. In some implementations, the device may perform the optical measurement based on the electrical measurement. In some implementations, the device may perform the optical measurement when the plurality of electrical probes are in contact with the human body, based on a resistance determined using the plurality of electrical probes. In some implementations, the device may perform the electrical measurement based on the optical measurement. In some implementations, the barrier may be between an illuminator and an optical detector of the optical sensor.

In some implementations, the optical sensor may be a first optical sensor and the at least one other sensor may be a second optical sensor. In some implementations, the first optical sensor may be associated with a first spectral range, and the second optical sensor may be associated with a second spectral range, where the first spectral range is different from the second spectral range. In some implementations, the first spectral range may be between approximately 400 nanometers and 1100 nanometers, and the second spectral range may have a lower bound equal to or greater than approximately 2500 nanometers.

In some implementations, an optical detector of the first optical sensor may be composed of a first material, and an optical detector of the second optical sensor may be composed of a second material different than the first material. In some implementations, the optical detector of the second optical sensor may be smaller than the optical detector of the first optical sensor.

In some implementations, the handheld or wearable sensor device may include a light pipe to transmit light from the surface to an optical detector of the second optical sensor. In some implementations, the first optical sensor may be associated with a first illuminator and the second optical sensor may be associated with a second illuminator different than the first illuminator. In some implementations, the at least one other sensor may include at least one of a temperature sensor, an electrical sensor, a magnetic sensor, a microbolometer, a barometric sensor, or an elasticity sensor.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like, depending on the context.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods described herein are without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items, and unrelated items, etc.), and may be used interchangeably with "one or more." Where only one item is intended, the term "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
   an optical sensor,
      wherein the optical sensor is to perform an optical measurement when a surface of the device is in contact with a human body; and
   a plurality of electrical probes,
      wherein an electrical probe, of the plurality of electrical probes, is provided in a barrier between an optical detector and an illuminator of the optical sensor,
      wherein the device is to perform an electrical measurement using the plurality of electrical probes when the surface of the device is in contact with the human body,
      wherein the electrical measurement is to be performed substantially contemporaneously with the optical measurement, and
      wherein the device is a handheld or wearable device.

2. The device of claim 1, wherein the electrical measurement is a hydration measurement or a resistance measurement.

3. The device of claim 1, wherein the device is to perform the optical measurement based on the electrical measurement.

4. The device of claim 1, wherein the device is to perform the optical measurement when the plurality of electrical probes are in contact with the human body based on a resistance determined using the plurality of electrical probes.

5. The device of claim 1, wherein the device is to perform the electrical measurement based on the optical measurement.

6. The device of claim 1, wherein the electrical probe is provided approximately in a center of the barrier.

7. A handheld or wearable sensor device, comprising:
   an optical sensor,
      wherein the optical sensor is to perform an optical health-related measurement when a surface of the handheld or wearable sensor device is in contact with a human body; and
   at least one other sensor provided in one or more corners of a physical shell of a housing of the optical sensor,
      wherein the at least one other sensor is to perform another health-related measurement, substantially contemporaneously with the optical health-related measurement or with a known time offset from the optical health-related measurement, when the surface of the handheld or wearable sensor device is in contact with the human body.

8. The handheld or wearable sensor device of claim 7, wherein the optical sensor is a first optical sensor and the at least one other sensor is a second optical sensor.

9. The handheld or wearable sensor device of claim 8, wherein the first optical sensor is associated with a first spectral range, and wherein the second optical sensor is associated with a second spectral range, wherein the first spectral range is different than the second spectral range.

10. The handheld or wearable sensor device of claim 9, wherein the first spectral range is between approximately 400 nanometers and 1100 nanometers, and wherein the second spectral range has a lower bound equal to or greater than approximately 2500 nanometers.

11. The handheld or wearable sensor device of claim 8, wherein an optical detector of the first optical sensor is composed of a first material, and wherein an optical detector of the second optical sensor is composed of a second material different than the first material.

12. The handheld or wearable sensor device of claim 11, wherein the optical detector of the second optical sensor is smaller than the optical detector of the first optical sensor.

13. The handheld or wearable sensor device of claim 8, further comprising:
   a light pipe to transmit light from the surface to an optical detector of the second optical sensor.

14. The handheld or wearable sensor device of claim 8, wherein the first optical sensor is associated with a first illuminator and the second optical sensor is associated with a second illuminator different than the first illuminator.

15. The handheld or wearable sensor device of claim 7, wherein the at least one other sensor includes at least one of:
   a temperature sensor,
   an electrical sensor,
   a magnetic sensor,
   a microbolometer,
   a barometric sensor, or
   an elasticity sensor.

16. A method performed by a multi-sensor device, comprising:
   performing an optical measurement using an optical sensor of the multi-sensor device,
      wherein the optical measurement is performed when a surface of the multi-sensor device is in contact with a human body; and
   performing another measurement using at least one other sensor of the multi-sensor device,
      wherein the at least one other sensor is in a barrier between an optical detector and an illuminator of the optical sensor,
      wherein the other measurement is performed when the surface of the multi-sensor device is in contact with the human body, wherein the other measurement is performed substantially contemporaneously with the optical measurement, and wherein the optical measurement and the other measurement relate to health parameters; and determining a combined measurement value based on the optical measurement and the other measurement.

17. The method of claim 16, further comprising:

identifying a region of interest for the other measurement using the optical measurement, wherein the other measurement is performed with regard to the region of interest.

18. The method of claim 16, wherein the optical measurement and the other measurement are performed based on a time offset between the optical measurement and the other measurement or a configurable time window in which the optical measurement and the other measurement are to be performed.

19. The method of claim 16, wherein performing the other measurement is based on the optical measurement.

20. The method of claim 16, further comprising:

determining that the surface of the multi-sensor device is in contact with the human body using the at least one other sensor, wherein performing the optical measurement is based on determining that the surface of the multi-sensor device is in contact with the human body.

* * * * *